(12) United States Patent
White et al.

(10) Patent No.: US 11,278,417 B2
(45) Date of Patent: Mar. 22, 2022

(54) ORTHOPAEDIC SYSTEM WITH MEDIAL PIVOTING INSERT

(71) Applicant: WM Innovations, LLC, Stanford, CA (US)

(72) Inventors: Stephen E. White, Fort Wayne, IN (US); William J. Maloney, Palo Alto, CA (US)

(73) Assignee: WM Innovations, LLC, Stanford, CA (US)

(*) Notice: Subject to any disclaimer, the term of this patent is extended or adjusted under 35 U.S.C. 154(b) by 0 days.

(21) Appl. No.: 16/802,091

(22) Filed: Feb. 26, 2020

(65) Prior Publication Data

US 2020/0268519 A1 Aug. 27, 2020

Related U.S. Application Data

(60) Provisional application No. 62/810,570, filed on Feb. 26, 2019.

(51) Int. Cl.
*A61F 2/38* (2006.01)
*A61F 2/28* (2006.01)
*A61F 2/30* (2006.01)
*A61F 2/08* (2006.01)

(52) U.S. Cl.
CPC .......... *A61F 2/3872* (2013.01); *A61F 2/3859* (2013.01); *A61F 2310/00017* (2013.01); *A61F 2310/00023* (2013.01); *A61F 2310/00029* (2013.01)

(58) Field of Classification Search
CPC combination set(s) only.
See application file for complete search history.

(56) References Cited

U.S. PATENT DOCUMENTS

| 2013/0018477 A1* | 1/2013 | Muratoglu | A61F 2/3836 623/20.28 |
| 2013/0173010 A1* | 7/2013 | Irwin | A61F 2/38 623/20.32 |
| 2015/0081029 A1* | 3/2015 | Bojarski | A61B 17/1675 623/20.32 |
| 2017/0079801 A1* | 3/2017 | Drury | A61F 2/38 |

* cited by examiner

*Primary Examiner* — Ann Schillinger
(74) *Attorney, Agent, or Firm* — Taylor IP, P.C.

(57) ABSTRACT

An orthopaedic system includes an insert defining an anterior-posterior centerline and including: a medial half on one side of the centerline and defining a medial shape, the medial half having a medial articular surface defining a medial dwell region; and a lateral half on an opposite side of the centerline and defining a lateral shape that differs from the medial shape, the lateral half having a lateral articular surface. A femoral component includes a medial condylar portion bearing on the medial articular surface and a lateral condylar portion bearing on the lateral articular surface. The insert is configured to substantially limit medial anterior-posterior translation on the femoral component and define a pivot axis that extends through the medial dwell region. The insert is configured such that rotation of the lateral articular surface follows an arcuate path about the pivot axis.

14 Claims, 7 Drawing Sheets

ORTHOPAEDIC SYSTEM WITH MEDIAL PIVOTING INSERT

CROSS REFERENCE TO RELATED APPLICATIONS

This is a non-provisional application based upon U.S. provisional patent application Ser. No. 62/810,570, entitled "ORTHOPAEDIC SYSTEM WITH MEDIAL PIVOTING INSERT", filed Feb. 26, 2019, which is incorporated herein by reference.

BACKGROUND OF THE INVENTION

1. Field of the Invention

The present invention relates to orthopaedic systems, and, more particularly, to orthopaedic systems for performing knee replacement surgery.

2. Description of the Related Art

Orthopaedic systems are known that are used to improve functions of joints in the body, such as the knee, that have been diminished due to injury and/or disease. For repairing the knee, an orthopaedic system may include an insert that is coupled to the tibia and a femoral component that is coupled to the femur. The femoral component bears on the insert to mimic the natural movement of the knee. While many orthopaedic systems provide the patient with a functional knee, known orthopaedic systems often have dynamic characteristics that do not mimic the natural knee.

What is needed in the art is an orthopaedic system that can closely mimic the natural movement of the knee following implantation.

SUMMARY OF THE INVENTION

The present invention provides an orthopaedic system with an insert that is asymmetric to allow medial pivoting that closely mimics the natural movement of the knee.

In some exemplary embodiments provided according to the present invention, an orthopaedic system includes an insert defining an anterior-posterior centerline and including: a medial half on one side of the centerline and defining a medial shape, the medial half having a medial articular surface defining a medial dwell region; and a lateral half on an opposite side of the centerline and defining a lateral shape that differs from the medial shape, the lateral half having a lateral articular surface. A femoral component includes a medial condylar portion bearing on the medial articular surface and a lateral condylar portion bearing on the lateral articular surface. The insert is configured to substantially limit medial anterior-posterior translation on the femoral component and define a pivot axis that extends through the medial dwell region. The insert is configured such that rotation of the lateral articular surface follows an arcuate path about the pivot axis.

One possible advantage that may be realized by exemplary embodiments provided according to the present invention is that rotation of the femoral component closely mimics the natural movement of the knee.

Another possible advantage that may be realized by exemplary embodiments provided according to the present invention is that the insert stabilizes the femoral component in the anterior-posterior direction to reduce the risk of implant shift.

Yet another possible advantage that may be realized by exemplary embodiments provided according to the present invention is that both internal and external rotation can occur over a defined rotation range without impingement by the insert on the condylar portions of the femoral component.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Referring now to the drawings, and more particularly to FIGS. 1-5, there is shown an exemplary embodiment of an orthopaedic system 100 for repairing a knee that generally includes an insert 200 and a femoral component 300 bearing on the insert 200. The insert 200 and the femoral component 300 may both comprise one or more biocompatible materials including, but not limited to, titanium, stainless steel, cobalt chrome, ultra-high molecular weight polyethylene, and polyether ether ketone. As can be seen, the femoral component 300 includes a pair of condylar portions 310, 320 that bear on the insert 200. The condylar portion 310 is, for example, a medial condylar portion that bears on a respective medial half 210 of the insert 200, as will be described further herein. Similarly, the condylar portion 320 may be a lateral condylar portion that bears on a respective lateral half 220 of the insert 200. Many different types of femoral components 300 are known, and any suitable configuration of femoral component may be incorporated in the orthopaedic system 100 provided in accordance with the present disclosure. With further reference to FIGS. 1-5, and referring now to FIGS. 6-13 as well, it can be seen that the insert 200 defines an anterior-posterior centerline CL (most clearly illustrated in FIGS. 6 and 9) that extends from an anterior 230 of the insert 200 to a posterior 240. The medial half 210 of the insert 200 is located on a medial side of the centerline CL and the lateral half 220 of the insert 200 is located on an opposite, lateral side of the centerline CL. As illustrated in, for example, FIG. 6, the halves 210, 220 of the insert 200 are asymmetrical, i.e., the medial half 210 and the lateral half 220 are not mirror images of each other.

Figure 8:
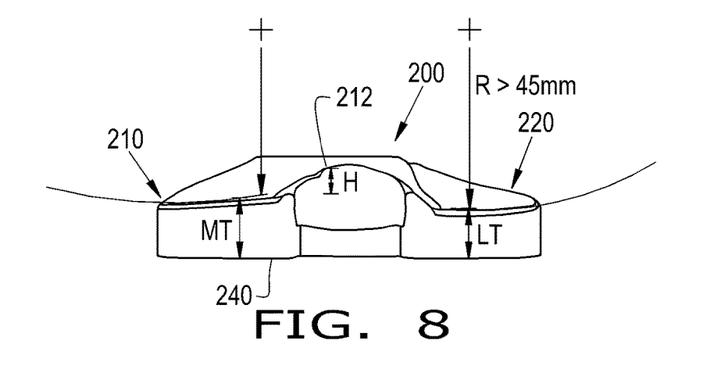
FIG. 8 is a posterior view of the insert of FIGS. 1-7.

The medial half 210 has a medial articular surface 211 and the lateral half 220 has a lateral articular surface 221. When the orthopaedic system 100 is formed, the medial condylar portion 310 of the femoral component 300 has a medial condylar surface 312 that bears on the medial articular surface 211 and the lateral condylar portion 320 has a lateral condylar surface 322 that bears on the lateral articular surface 221. The medial articular surface 211, the medial condylar surface 312, the lateral articular surface 221, and the lateral condylar surface 322 may each be generally flat in the medial-lateral direction. As used herein, "generally flat" corresponds to a radius in the medial-lateral direction ML of at least 45 mm, as illustrated in FIG. 8. Further, each of the surfaces 211, 312, 221, 322 may be dished in an anterior-posterior direction AP in the sense that the surfaces 211, 312, 221, 322 define a radius in the anterior-posterior direction AP that is less than 45 mm. In other words, the medial curvature of the surfaces 211, 312, 221, 322 in the medial-lateral direction ML is less than the anterior curvature in the anterior-posterior direction AP because the radius in the medial-lateral direction is greater than the radius in the anterior-posterior direction AP. Further, both condylar portions 310, 320 may be non-spherically curved and instead be, for example, cylindrically curved.

Figure 1:
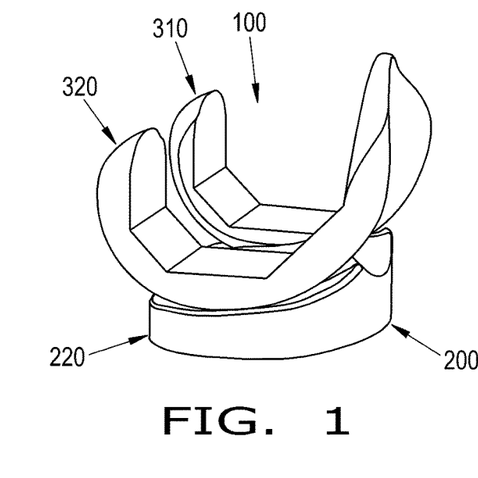
FIG. 1 is a perspective view from a lateral side of an orthopaedic system including an insert and a femoral component bearing on the insert, provided in accordance with the present invention.
Figure 2:
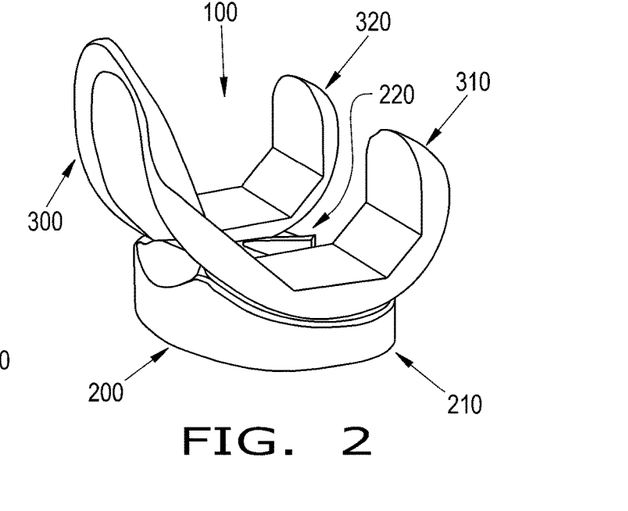
FIG. 2 is a perspective view from a medial side of the orthopaedic system of FIG. 1.
Figure 3:
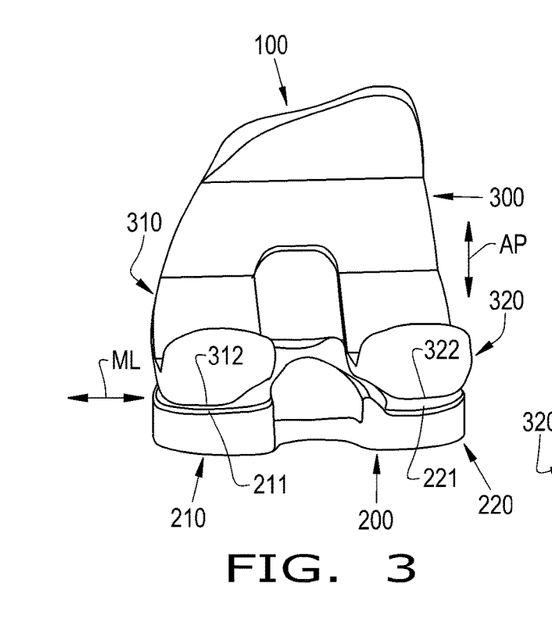
FIG. 3 is a posterior perspective view of the orthopaedic system of FIGS. 1-2.
Figure 4:
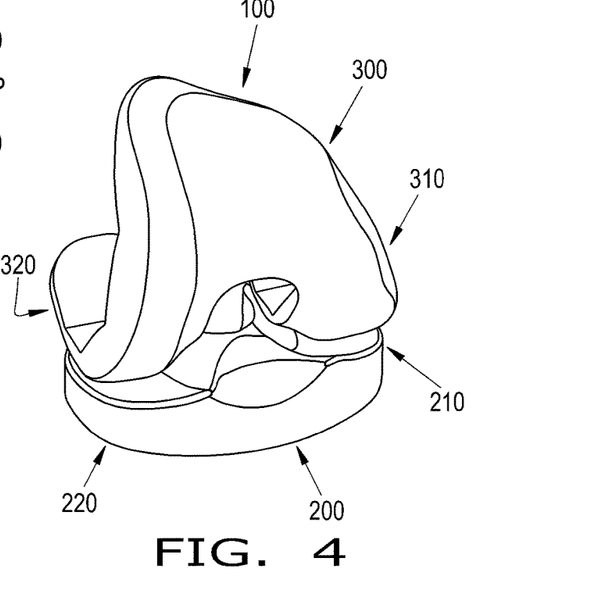
FIG. 4 is a perspective view from the anterior of the orthopaedic system of FIGS. 1-3.
Figure 5:
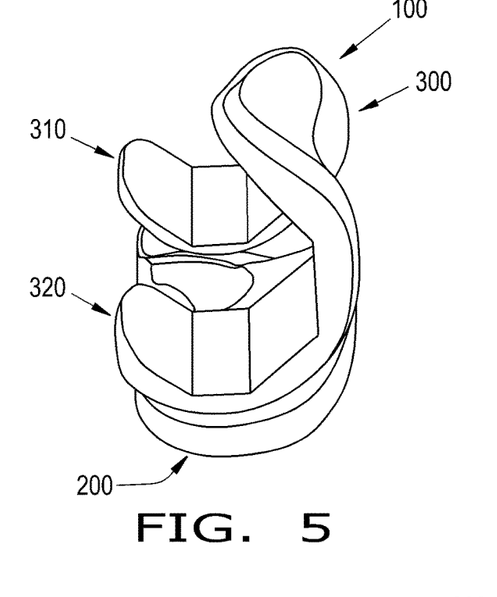
FIG. 5 is another perspective view of the orthopaedic system of FIGS. 1-4.
Figure 6:
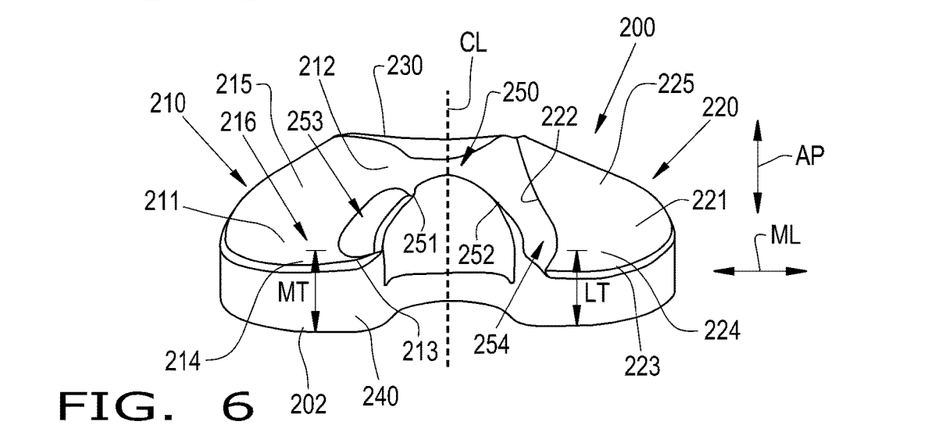
FIG. 6 is a perspective view of the posterior of the insert of the orthopaedic system of FIGS. 1-5.
Figure 7:
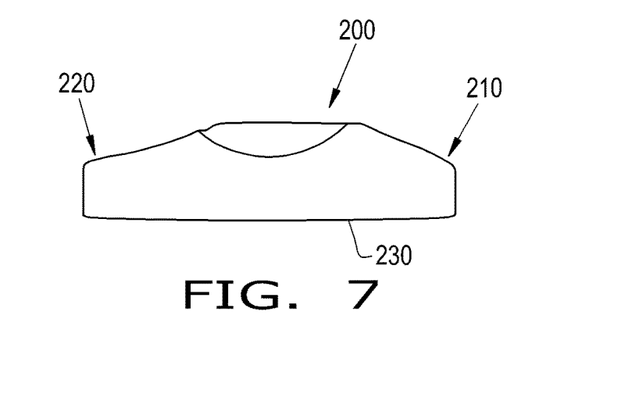
FIG. 7 is an anterior view of the insert of FIGS. 1-6.

The medial articular surface 211 may include a medial valley 214 with a medial dwell region 216 defining a medial minimum thickness MT and the lateral articular surface 221 may include a lateral valley 224 defining a lateral minimum thickness LT that is less than the medial minimum thickness MT, which may be seen in FIGS. 6 and 8. It should be appreciated that the shapes of the articular surfaces 211, 221 may be adjusted, as desired and/or necessary, to accommodate differently shaped femoral components and/or patient anatomy, as is known in the art. Thus, it should be appreciated that the insert 200 and the femoral component 300 provided according to the present invention can be modified in a large variety of ways.

The insert 200 is configured to substantially limit medial anterior-posterior translation in the anterior-posterior direction AP. In other words, the orthopaedic system 100 is stabilized in the anterior-posterior direction AP so little, if any, translation of the insert 200 and femoral component 300 occur in the anterior-posterior direction AP until deeper flexion angles of the knee. The shape of the insert 200 is provided so a pivot axis PA (illustrated in FIG. 13) extends through the medial dwell region 216 in the medial articular surface 211. By placing the pivot axis PA through the medial dwell region 216 on the medial half 210, rotation of the lateral articular surface 221 follows an arcuate path A about the pivot axis PA while still allowing translation of the lateral articular surface 221 about the medial dwell region 216. In this respect, rotation of the orthopaedic system 100 closely mimics that of the natural knee, which exhibits a medial pivot a majority of the time.

One known implant system, commercially sold as the TRIATHLON® system by STRYKER®, is commonly used for knee repair. While the TRIATHLON® system provides stability in the medial-lateral direction, there is minimal stability in the anterior-posterior direction. The lack of stability in the anterior-posterior direction increases the feel of instability to the patient.

To substantially limit medial anterior-posterior translation, an anterior portion of the medial articular surface 211 of the insert 200 provided according to the present invention is shaped to closely conform with a corresponding anterior portion of the medial condylar surface 312. This conformity between the surfaces 211 and 312 limits medial anterior-posterior translation and thus provides significant stability in the anterior-posterior direction AP without having to utilize, for example, a post. The lateral articular surface 221, on the other hand, may be less conforming to the lateral condylar surface 322 to promote pivoting along the arcuate path A.

Figure 11:
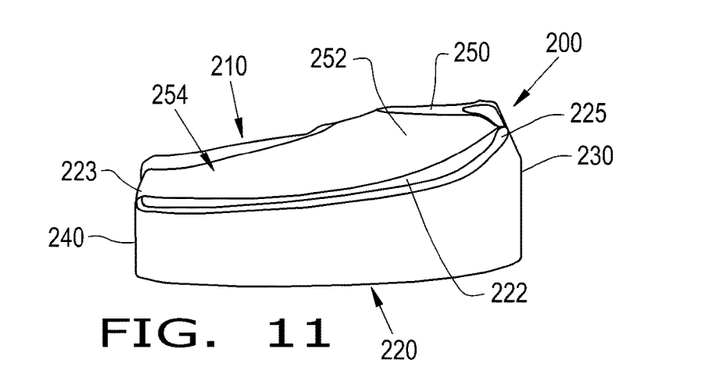
FIG. 11 is a lateral view of the insert of FIGS. 1-10.
Figure 12:
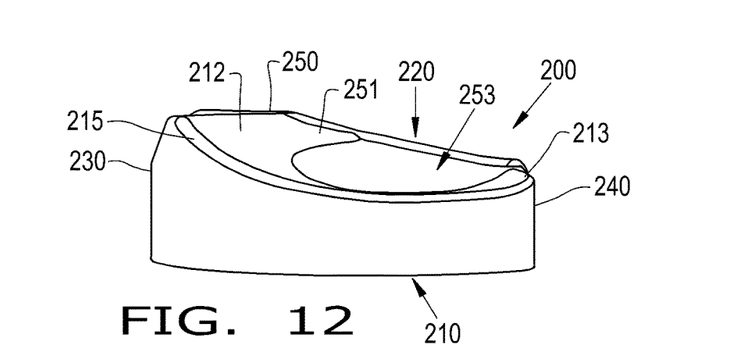
FIG. 12 is a medial view of the insert of FIGS. 1-11.
Figure 13:
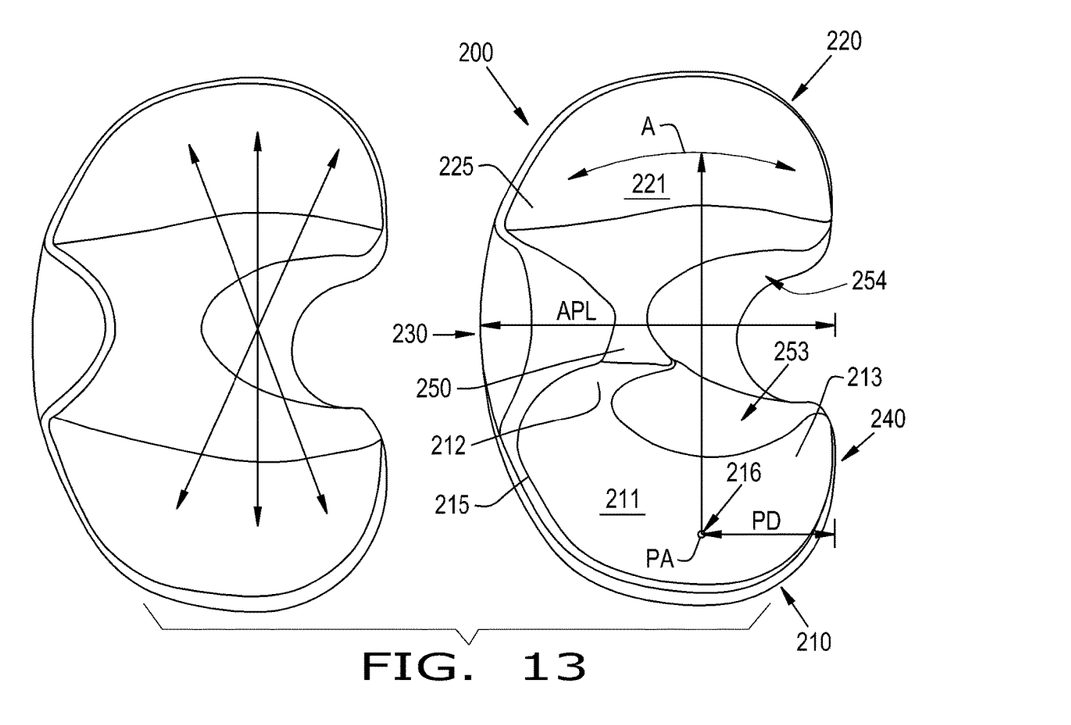
FIG. 13 is a top view of the insert of FIGS. 1-12 with arrows illustrating pivoting movement of the insert provided according to the present invention compared to an insert configured for center pivoting movement of a femoral component.

Referring specifically now to FIGS. 11 and 12, anterior stabilizing surfaces 215, 225 formed in the halves 210, 220 of the insert 200 are illustrated in further detail. The anterior stabilizing surfaces 215, 225 may be formed as sloped surfaces that extends downwardly toward the posterior 240 at a slope angle of between 4° and 8° such as, for example, a 6° slope angle. The anterior stabilizing surfaces 215, 225 may be formed adjacent to the anterior 230 of the insert 200 and brace the femoral component 300 against anterior-posterior movement, as can be appreciated from FIGS. 1 and 2. This further stabilization against anterior-posterior translation can reduce the risk of the implant system 100 failing following implantation.

Figure 9:
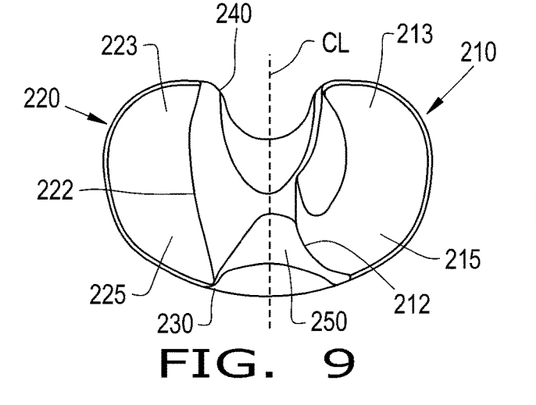
FIG. 9 is a top view of the insert of FIGS. 1-8.
Figure 10:
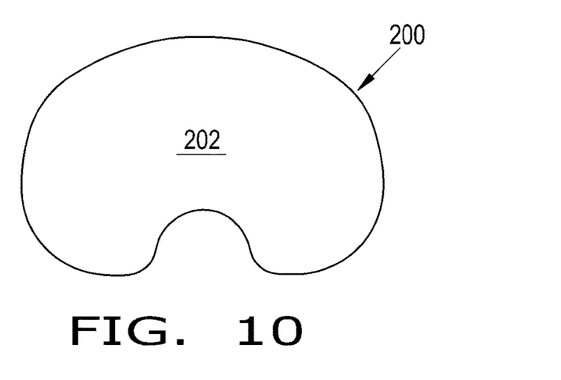
FIG. 10 is a bottom view of the insert of FIGS. 1-9.

Referring still to FIGS. 1-13, the medial half 210 may be formed with a raised medial surface 212 that defines a peak of the insert 200. The raised medial surface 212 may, for example, extend generally vertical relative to a bottom 202 of the insert 200 and conform to the medial condylar portion 310. The raised medial surface 212 may be located adjacent to the centerline CL near the anterior 230 of the insert 200. Material may be removed from the medial half 210, as illustrated in FIG. 9, to avoid impingement with the femoral component 300 during rotation, as will be described further herein. The raised medial surface 212 may define a height H, relative to the medial minimum thickness MT of the medial valley 214, that is at least 10 mm i.e., the raised medial surface 212 extends at least 10 mm above the lowest point of the medial valley 214. The raised medial surface 212 defining the height H can satisfy the "jumping distance" requirement of 10 mm, as is known, to prevent anterior dislocation of the insert 200 and the femoral component 300. The medial half 210 may also include a dished surface 213 adjacent to the posterior 240 of the insert 200 that has a curved dish formed therein.

The lateral half 220, in contrast to the medial half 210, may be formed with a generally smooth curved recess 222 that does not closely conform to the lateral condylar portion 320. The lateral half 220 may also have a dished surface 223 adjacent the centerline CL and near the posterior 240 of the insert 200. The lateral articular surface 221 may have a flat sagittal curvature. Thus, the lateral half 220 is shaped and configured to not conform closely with the lateral condylar portion 320, which encourages rotation of the lateral articular surface 221 along the arcuate path A about the pivot axis PA.

From the foregoing, it should be appreciated that the insert 200 provided in accordance with the present disclosure has a shape that locates the pivot axis PA through the medial dwell region 216 of the medial half 210 of the insert 200 due to asymmetry of the medial half 210 and the lateral half 220. In some embodiments, and referring now to FIG. 13, the insert 200 defines an anterior-to-posterior length APL between the anterior 230 and the posterior 240 and the pivot axis PA of the femoral component 300 is spaced from the posterior 240 by a pivot distance PD that is 32% to 37% of the anterior-to-posterior length APL, e.g., if the anterior-to-posterior length APL is 100 mm, the pivot axis PA may be spaced 32 cm to 37 cm from the posterior 240. By shaping the insert 200 to place the pivot axis PA in this area of the medial half 210, medial articulation (pivoting) can be relatively conforming and resist posterior-anterior translation following implantation. Medial pivoting of the lateral articular surface 221 along the arcuate path A about the pivot axis PA, as opposed to rotating motion about a central eminence that is common in known implants (shown on the left in FIG. 13), also is similar to the natural articulation of the knee and is less prone to generating unnatural stresses in the region that can lead to tissue damage and/or implant failure. Thus, the insert 200 provided according to the present invention can be utilized in the orthopaedic system 100 to allow a movement range that closely mimics the natural movement of the knee.

Figure 14:
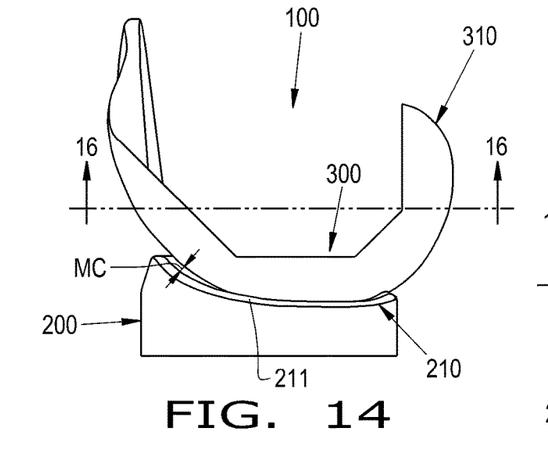
FIG. 14 is a medial view of the orthopaedic system of FIGS. 1-5.
Figure 15:
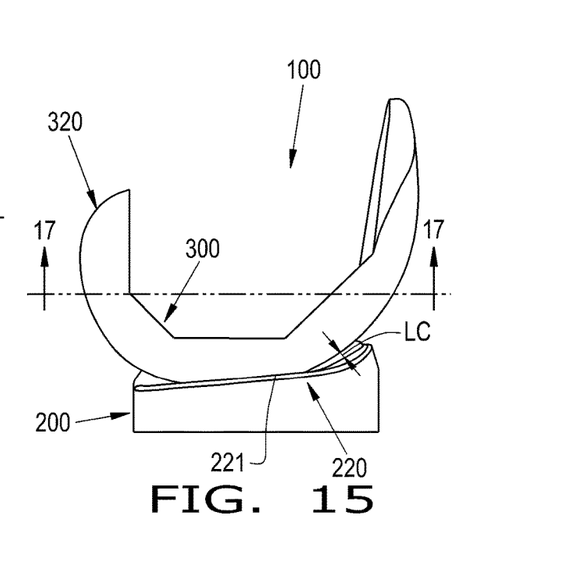
FIG. 15 is a lateral view of the orthopaedic system of FIGS. 1-5 and 14.
Figure 16:
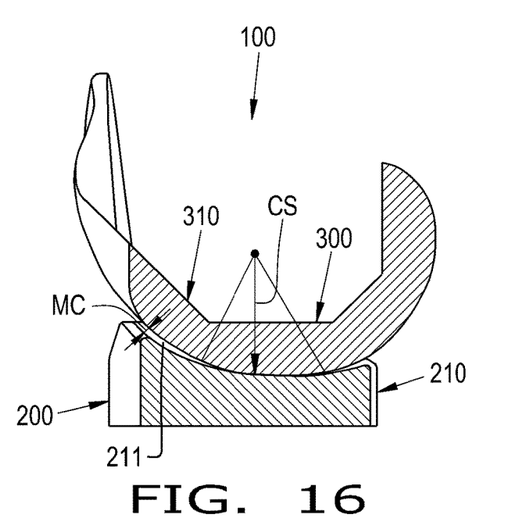
FIG. 16 is a cross-sectional view of the orthopaedic system of FIG. 14 taken along line 16-16.
Figure 17:
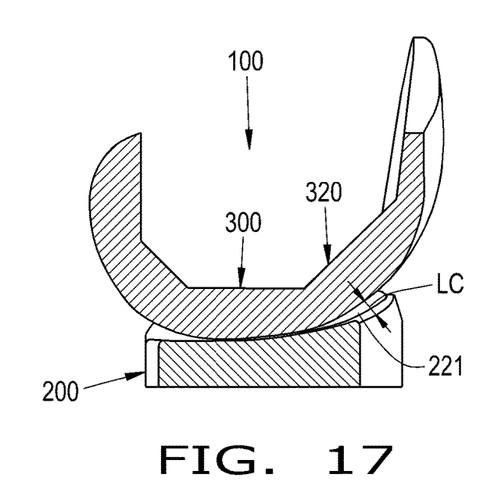
FIG. 17 is a cross-sectional view of the orthopaedic system of FIG. 15 taken along line 17-17.

Referring specifically now to FIGS. 14-17, various views of the orthopaedic system 100 provided according to the present invention are illustrated. As illustrated in FIGS. 14 and 16, the medial condylar portion 310 and the medial articular surface 211 define a maximum medial clearance MC therebetween. As illustrated in FIGS. 15 and 17, the lateral condylar portion 320 and the lateral articular surface 221 define a maximum lateral clearance LC therebetween. As can be appreciated from comparing FIGS. 14 and 16 to FIGS. 15 and 17, the maximum lateral clearance LC may be greater than the maximum medial clearance MC due to the insert 200 being shaped so the medial articular surface 211 conforms closely to the shape of the medial condylar portion 310 while the lateral articular surface 221 is less conforming to the shape of the lateral condylar portion 320. The close conforming between the medial articular surface 211 and the medial condylar portion 310 helps provide the previously described medial pivoting characteristics.

Figure 18:
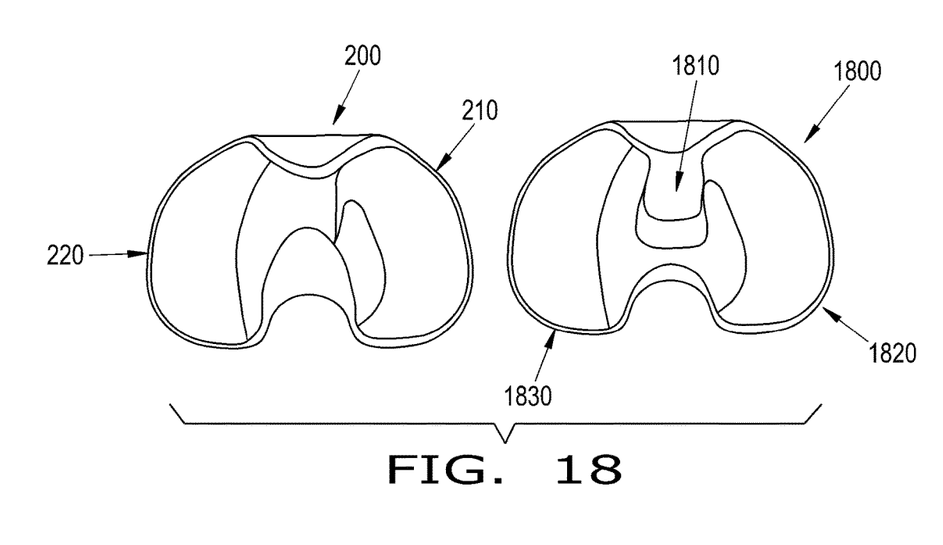
FIG. 18 is a perspective view of various inserts for an orthopaedic system.

In some embodiments, and referring now to FIG. 18, an insert 1800 is provided that is similar to the previously described insert 200 but includes a post 1810 formed near a center of the insert 1800. For comparison, the insert 200 is also illustrated in FIG. 18. The post 1810 may be formed, for example, by removing material from the center of the insert 1800 while maintaining asymmetry between a medial side 1820 and a lateral side 1830 of the insert 1800. The post 1810 may be shaped to engage a corresponding cam formed in a femoral component that bears on the insert 1800, similarly to known orthopaedic systems with posts. In other respects, the insert 1800 may be similar to the insert 200, so further description is omitted for brevity.

Figure 19:
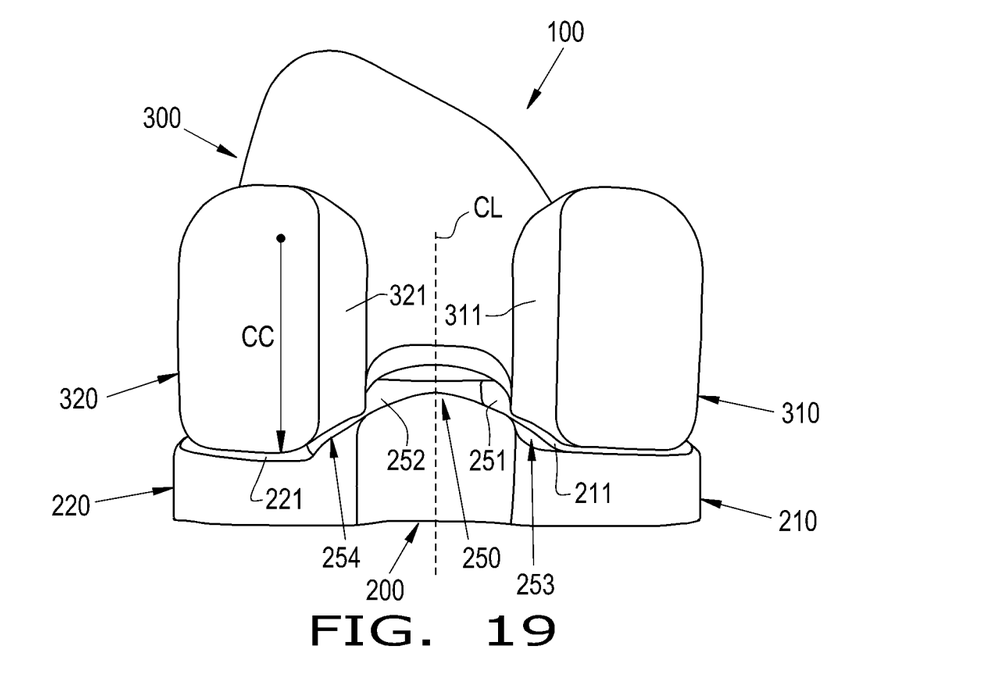
FIG. 19 is a close-up posterior view of the orthopaedic system of FIGS. 1-5 and 14-17.

Referring now to FIG. 19, a close-up posterior view of the orthopaedic system 100 is illustrated. As illustrated, each of the condylar portions 310, 320 of the femoral component 300 may have a corresponding concave patellar groove 311, 321 that extends through its respective condylar portion 310, 320. As can be appreciated from FIG. 19, the patellar grooves 311, 321 may articulate and interact with the respective articular surfaces 211, 221 of the insert 200 throughout movement of the orthopaedic system 100. The patellar groove 311 of the medial condylar portion 310 may closely conform to the medial articular surface 211, to provide the medial pivot movement, while the patellar groove 321 of the lateral condylar portion 320 less closely conforms to the lateral articular surface 221 to allow pivoting along the arcuate path A. The femoral component 300 may define a sagittal curvature CS (illustrated in FIG. 16) of no more than 40 mm and a coronal curvature CC (illustrated in FIG. 19) of no more than 45 mm. Further, the sagittal and coronal shapes of the femoral component 300, in some embodiments, are not spherical. By shaping the femoral component 300 in this manner, the orthopaedic system 100 can allow normal flexion while still providing medial pivoting.

As can be appreciated from FIG. 19, the insert 200 has a central ridge 250 with a medial ridge portion 251 on the medial half 210 and a lateral ridge portion 252 on the lateral half 220. The medial ridge portion 251 has a different shape than the lateral ridge portion 252, as will be described further herein. The concave patellar groove 311 of the medial condylar portion 310 faces the medial ridge portion 251 and the concave patellar groove 321 of the lateral condylar portion 320 faces the lateral ridge portion 252 for articulation. The medial ridge portion 251 has a region 253 formed therein that has less material than a corresponding region 254 of the lateral ridge portion 252 on the opposite side of the anterior-posterior centerline CL, i.e., the region 253 of the medial ridge portion 251 is not a mirror of the region 254 of the lateral ridge portion 252, but has a recess or divot formed therein.

By forming the region 253 of the medial ridge portion 251 with less material than the corresponding region 254 of the lateral ridge portion 252, external rotation is not undesirably prohibited by impingement between the medial condylar portion 310 and the medial ridge portion 251 of the central ridge 250. This is in contrast to known orthopaedic systems, such as the previously described TRIATHLON® system, which have a symmetric central ridge. In such known designs, medial pivoting with combined anterior-posterior stability from close conformity would not be effective because the close conformity between the patellar groove of the medial condylar portion and the symmetric central ridge would interfere with rotation, i.e., the medial condylar portion would abut against the symmetric ridge during rotation and significantly shorten the rotation range. If the symmetric central ridge of known designs was modified to remove material that would impinge rotation, there would be a significant loss of medial-lateral stability during rotation of the lateral surfaces. The insert 200 provided according to the present invention, on the other hand, has an asymmetric central ridge 250 with material removed in the region 253 of the medial ridge portion 251, compared to the corresponding region 254 of the lateral ridge portion 252, so there is not impingement between the femoral component 300 and the central ridge 250 during the desired rotation range while maintaining the anterior-posterior stability from close conformity on the medial half 210. Thus, the region 253 of the medial ridge portion 251 is configured to avoid impingement of the central ridge 250 on the medial condylar portion 310 during rotation.

Figure 20A:
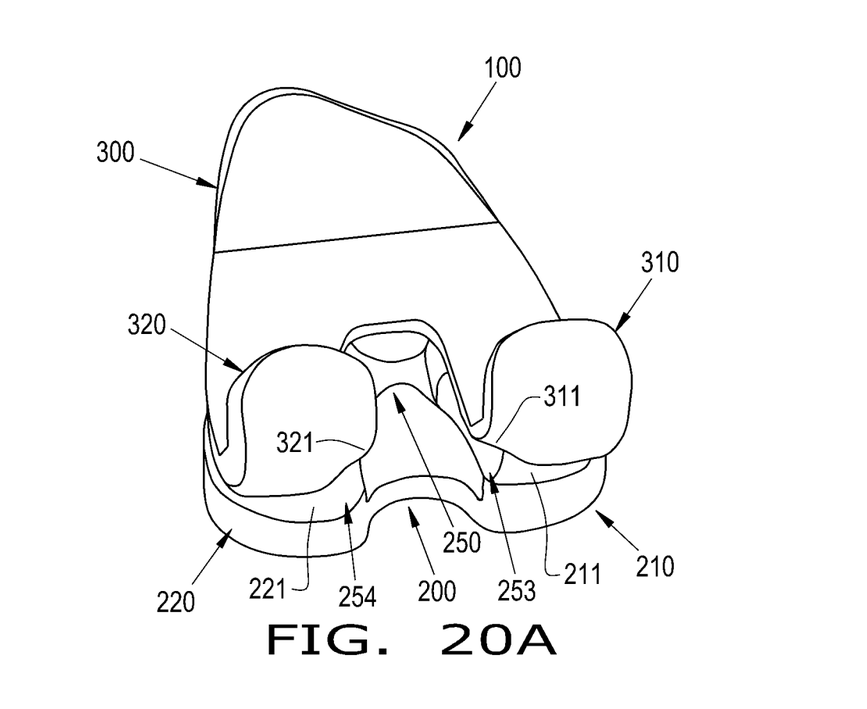
FIG. 20A is a perspective view of the orthopaedic system of FIGS. 1-5, 14-17, and 19 in a neutral, non-pivoted position.
Figure 20B:
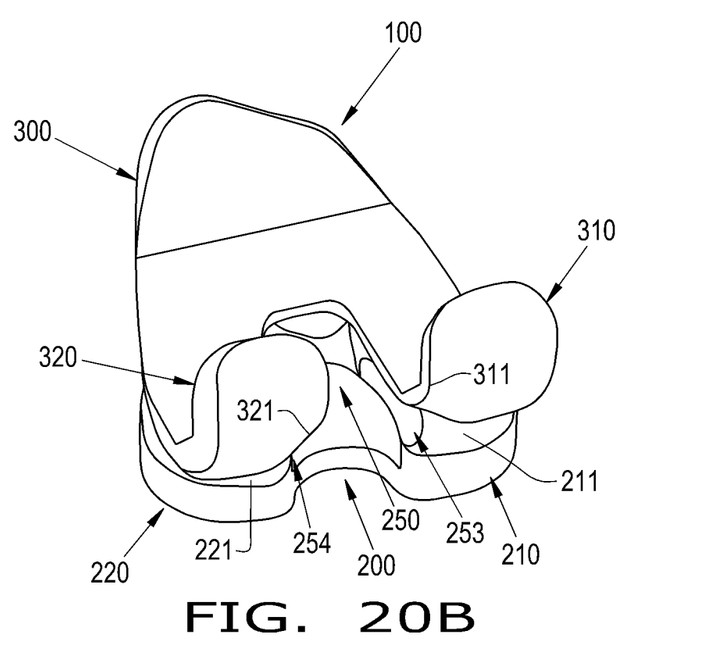
FIG. 20B is a perspective view of the orthopaedic system of FIG. 20A after 13° of external pivoting.
Figure 20C:
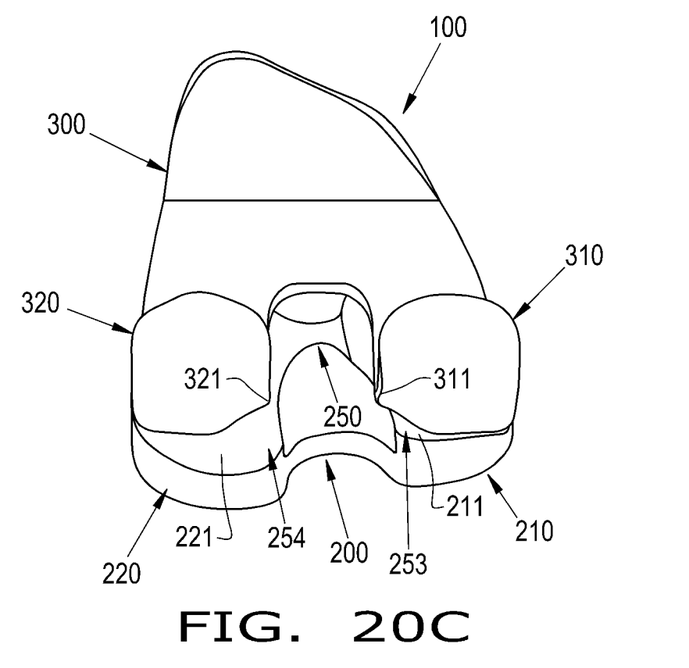
FIG. 20C is a perspective view of the orthopaedic system of FIG. 20A after 10° of internal pivoting.

Referring now to FIGS. 20A-20C, the orthopaedic system 100 is illustrated in various stages of pivoting. FIG. 20A illustrates the orthopaedic system 100 in a neutral position where there has been no pivoting, i.e., there is 0° of pivoting. FIG. 20B, on the other hand, illustrates the orthopaedic system 100 after 13° of posterior pivoting (which may also be called "external pivoting"). As can be appreciated from FIG. 20B, compared to FIG. 20A, pivoting of the lateral articular surface 321 has followed the arcuate path A about the pivot axis PA. FIG. 20C illustrates the orthopaedic system 100 after 10° of anterior pivoting (which may also be called "internal pivoting"). Similarly to FIG. 20B, it can be seen in FIG. 20C that the lateral articular surface 221 has followed the arcuate path A about the pivot axis PA. Due to there being less material in the region 253 of the medial ridge portion 251 than the corresponding region 254 of the lateral ridge portion 252, both internal and external rotation are allowed across the desired range of rotation. In some embodiments, the femoral component 300 is limited to 25° of rotation about the pivot axis PA, i.e., the range of rotation is 25°. As can be appreciated from FIG. 20B, external rotation to the position in FIG. 20B would not be possible if the medial ridge portion 251 had the same shape as the lateral ridge portion 252, i.e., more material in the region 253, because the patellar groove 311 of the medial condylar portion 310 would abut against the medial ridge portion 251 and prevent further rotation. Thus, the medial ridge portion 251 being a different shape than the lateral ridge portion 252 allows close conforming between the medial condylar portion 310 and the medial articular surface 311 to provide anterior-posterior stability and medial pivoting without interfering with the natural range of rotation.

From the foregoing, it should be appreciated the orthopaedic system 100 provided according to the present invention provides a medial pivoting implant system that has improved anterior-posterior stability due to close conforming between the medial condylar portion 310 and the medial articular surface 211 while still allowing the natural range of rotation of the knee. The shape of the medial half 210 is different than the shape of the lateral half 220 to provide the described location of the medial dwell region 216 and close conformity for medial pivoting and also eliminates the presence of material that would obstruct external rotation. Thus, the orthopaedic system 100 provided according to the present invention allows natural movement of the knee while improving anterior-posterior stability.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic system, comprising:
an insert defining an anterior-posterior centerline and comprising:
a medial half on one side of the centerline and defining a medial shape, the medial half comprising a medial articular surface defining a medial dwell region; and
a lateral half on an opposite side of the centerline and defining a lateral shape that differs from the medial shape, the lateral half comprising a lateral articular surface; and
a femoral component comprising a medial condylar portion bearing on the medial articular surface and a lateral condylar portion bearing on the lateral articular surface, the insert being configured to substantially limit anterior-posterior translation of the femoral component and define a pivot axis that extends through the medial dwell region, the insert being configured such that rotation of the lateral articular surface follows an arcuate path about the pivot axis, wherein the insert comprises a central ridge including a lateral ridge portion on the lateral half and a medial ridge portion on the medial half that has a different shape than the lateral ridge portion, the lateral condylar portion having a lateral concave patellar groove formed therein that faces the lateral ridge portion and the medial condylar portion having a medial concave patellar groove formed therein that faces the medial ridge portion, the medial ridge portion having a region formed therein that has less material than a corresponding region of the lateral ridge portion.

2. The orthopaedic system of claim 1, wherein the region of the medial ridge portion is configured to avoid impingement of the central ridge on the medial condylar portion during external rotation.

3. The orthopaedic system of claim 2, wherein the femoral component is limited to 25 degrees of rotation about the pivot axis.

4. The orthopaedic system of claim 1, wherein the insert comprises an anterior and a posterior and defines an anterior-to-posterior length between the anterior and the posterior, wherein the pivot axis is spaced from the posterior of the insert by a pivot distance, the pivot distance being 32% to 37% of the anterior-to-posterior length.

5. The orthopaedic system of claim 1, wherein the medial condylar portion and the medial articular surface define a maximum medial clearance therebetween and the lateral condylar portion and the lateral articular surface define a maximum lateral clearance therebetween that is greater than the maximum medial clearance.

6. The orthopaedic system of claim 1, wherein the medial dwell region defines a medial minimum height and the lateral articular surface comprises a lateral valley defining a lateral minimum height that is less than the medial minimum height.

7. The orthopaedic system of claim 1, wherein the medial half comprises a raised medial surface defining a peak of the insert and extending generally vertical relative to a bottom of the insert.

8. The orthopaedic system of claim 7, wherein the raised medial surface is located adjacent to the anterior-posterior centerline.

9. The orthopaedic system of claim 7, wherein the medial half comprises a dished surface adjacent to a posterior of the insert, the dished surface having a curved dish formed therein.

10. The orthopaedic system of claim 1, wherein the insert further comprises an anterior stabilizing surface formed adjacent to an anterior of the insert and formed as a sloped surface that extends downwardly toward a posterior of the insert.

11. The orthopaedic system of claim 10, wherein the anterior stabilizing surface extends downwardly toward the posterior at a slope angle of between 4° and 8°.

12. The orthopaedic system of claim 1, wherein the medial condylar portion comprises a medial condylar surface bearing on the medial articular surface and the lateral condylar portion comprises a lateral condylar surface bearing on the lateral articular surface, wherein the medial articular surface, the medial condylar surface, the lateral condylar surface, and the lateral articular surface are each generally flat in a medial-lateral direction.

13. The orthopaedic system of claim 12, wherein the medial articular surface, the medial condylar surface, the lateral condylar surface, and the lateral articular surface are each dished in an anterior-posterior direction.

14. The orthopaedic system of claim 12, wherein the medial articular surface, the medial condylar surface, the lateral condylar surface, and the lateral articular surface each define a respective radius that is at least 45 mm in the medial-lateral direction.

* * * * *